United States Patent
Roeder et al.

(10) Patent No.: US 8,551,158 B2
(45) Date of Patent: Oct. 8, 2013

(54) STEERABLE ILIAC BRANCH DEVICE

(75) Inventors: Blayne A. Roeder, Lafayette, IN (US);
Matthew S. Huser, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/460,036

(22) Filed: Apr. 30, 2012

(65) Prior Publication Data
US 2012/0290068 A1 Nov. 15, 2012

Related U.S. Application Data

(60) Provisional application No. 61/485,813, filed on May 13, 2011.

(51) Int. Cl.
*A61F 2/06* (2013.01)

(52) U.S. Cl.
USPC ............ 623/1.35; 623/1.16; 606/41; 600/149

(58) Field of Classification Search
USPC ........... 623/1.11, 1.13–1.22, 1.35, 1.36, 23.7; 606/41; 600/149–150; 604/94.04
See application file for complete search history.

(56) References Cited

U.S. PATENT DOCUMENTS

| | | | |
|---|---|---|---|
| 4,796,607 A * | 1/1989 | Allred et al. ................... | 600/141 |
| 5,687,723 A * | 11/1997 | Avitall ........................... | 600/374 |
| 6,126,649 A * | 10/2000 | VanTassel et al. ............. | 604/528 |
| 7,160,318 B2 | 1/2007 | Greenberg et al. ........... | 623/1.13 |
| 7,407,509 B2 | 8/2008 | Greenberg et al. ........... | 623/1.35 |
| 7,435,253 B1 | 10/2008 | Hartley et al. ................. | 623/1.12 |
| 7,537,606 B2 | 5/2009 | Hartley et al. ................. | 623/1.11 |
| 7,846,194 B2 | 12/2010 | Hartley et al. ................. | 623/1.13 |
| 2003/0167083 A1* | 9/2003 | Lashinski et al. ............. | 623/1.12 |
| 2004/0098084 A1 | 5/2004 | Hartley et al. ................. | 623/1.11 |
| 2005/0113905 A1 | 5/2005 | Greenberg et al. ........... | 623/1.16 |
| 2005/0182476 A1 | 8/2005 | Hartley et al. ................. | 623/1.11 |
| 2006/0095118 A1 | 5/2006 | Hartley ......................... | 623/1.35 |
| 2006/0155363 A1* | 7/2006 | LaDuca et al. ................ | 623/1.16 |

(Continued)

FOREIGN PATENT DOCUMENTS

| EP | 1 847 236 A2 | 10/2007 |
|---|---|---|
| WO | WO 2007/084724 A2 | 7/2007 |

OTHER PUBLICATIONS

Extended European Search Report, dated Sep. 14, 2012, pp. 1-6, European Patent Application No. 12167752.0.

*Primary Examiner* — Paul Prebilic
(74) *Attorney, Agent, or Firm* — Brinks Hofer Gilson & Lione

(57) ABSTRACT

A prosthesis may be used for treatment of an aneurysmal body vessel. The prosthesis may include a prosthetic trunk and a prosthetic branch. The prosthetic trunk may include a graft body, an open first end, an open second end, and a trunk lumen extending therebetween. The prosthetic branch may include a graft body, an open first end, an open second end, and a branch lumen extending therebetween. The first end of the prosthetic branch may be attached to the prosthetic trunk, and the branch lumen may be in fluid communication with the trunk lumen. The prosthetic branch may be movable in relation to the prosthetic trunk between neutral, right biased, and left biased configurations. First and second releasable steering members may be associated with the respective first and second biased configurations and may cooperatively retain the prosthetic branch in the neutral configuration.

19 Claims, 8 Drawing Sheets

(56) References Cited

U.S. PATENT DOCUMENTS

| | | |
|---|---|---|
| 2008/0114438 A1 | 5/2008 | Hartley et al. ............... 623/1.11 |
| 2008/0114440 A1* | 5/2008 | Hlavka et al. ................ 623/1.12 |
| 2009/0099648 A1 | 4/2009 | Yu |
| 2009/0149939 A1 | 6/2009 | Godlewski et al. .......... 623/1.13 |
| 2009/0171451 A1 | 7/2009 | Kuppurathanam et al. .. 623/1.36 |
| 2009/0254170 A1 | 10/2009 | Hartley et al. ............... 623/1.12 |
| 2010/0063576 A1 | 3/2010 | Schaeffer et al. ............ 623/1.13 |
| 2010/0268327 A1 | 10/2010 | Bruszewski et al. ......... 623/1.18 |
| 2011/0054594 A1 | 3/2011 | Mayberry et al. ........... 623/1.34 |
| 2011/0313512 A1 | 12/2011 | Hartley et al. ............... 623/1.35 |

* cited by examiner

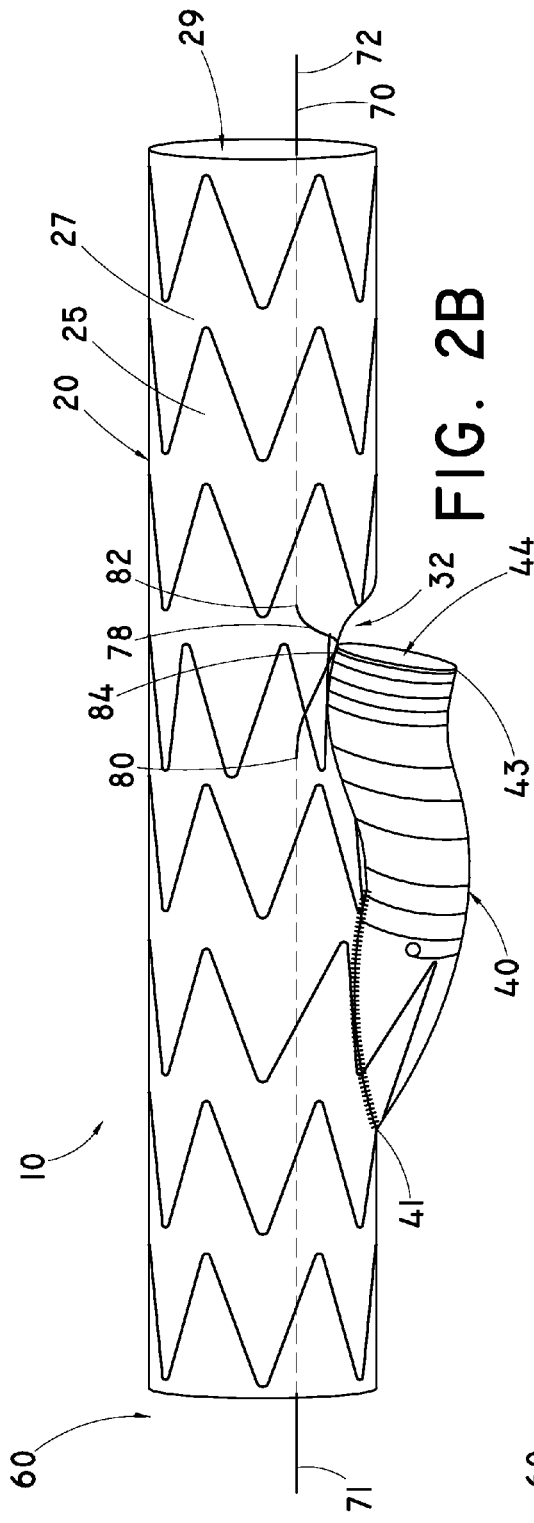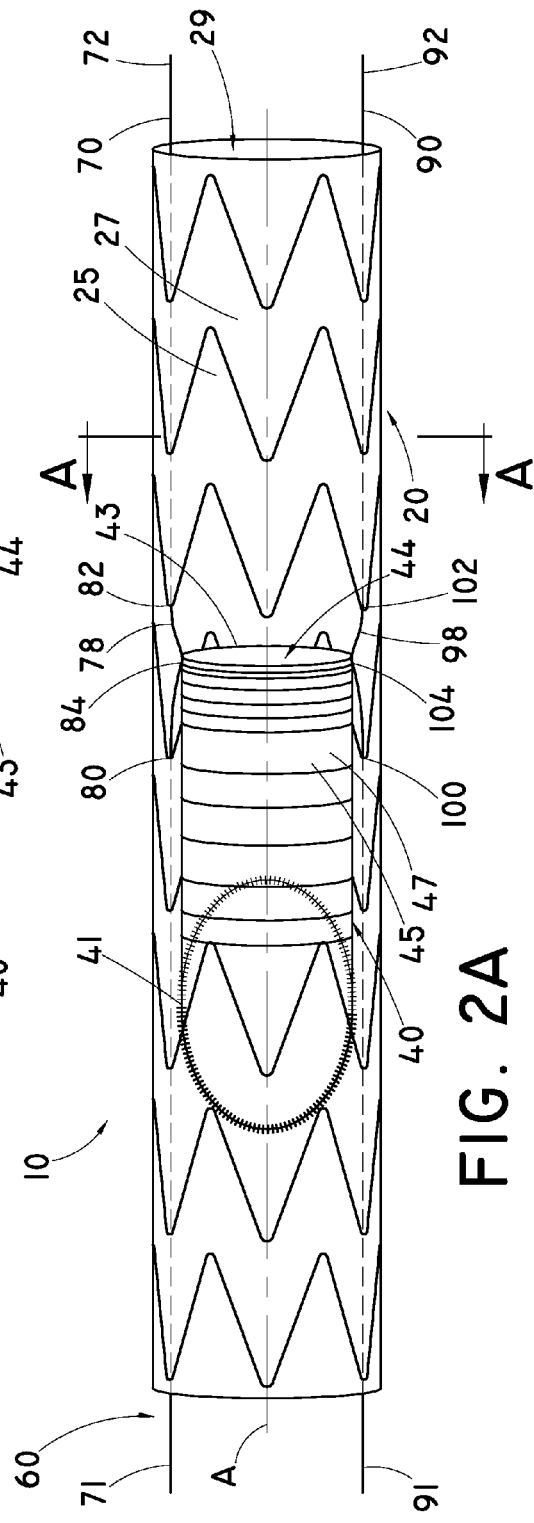

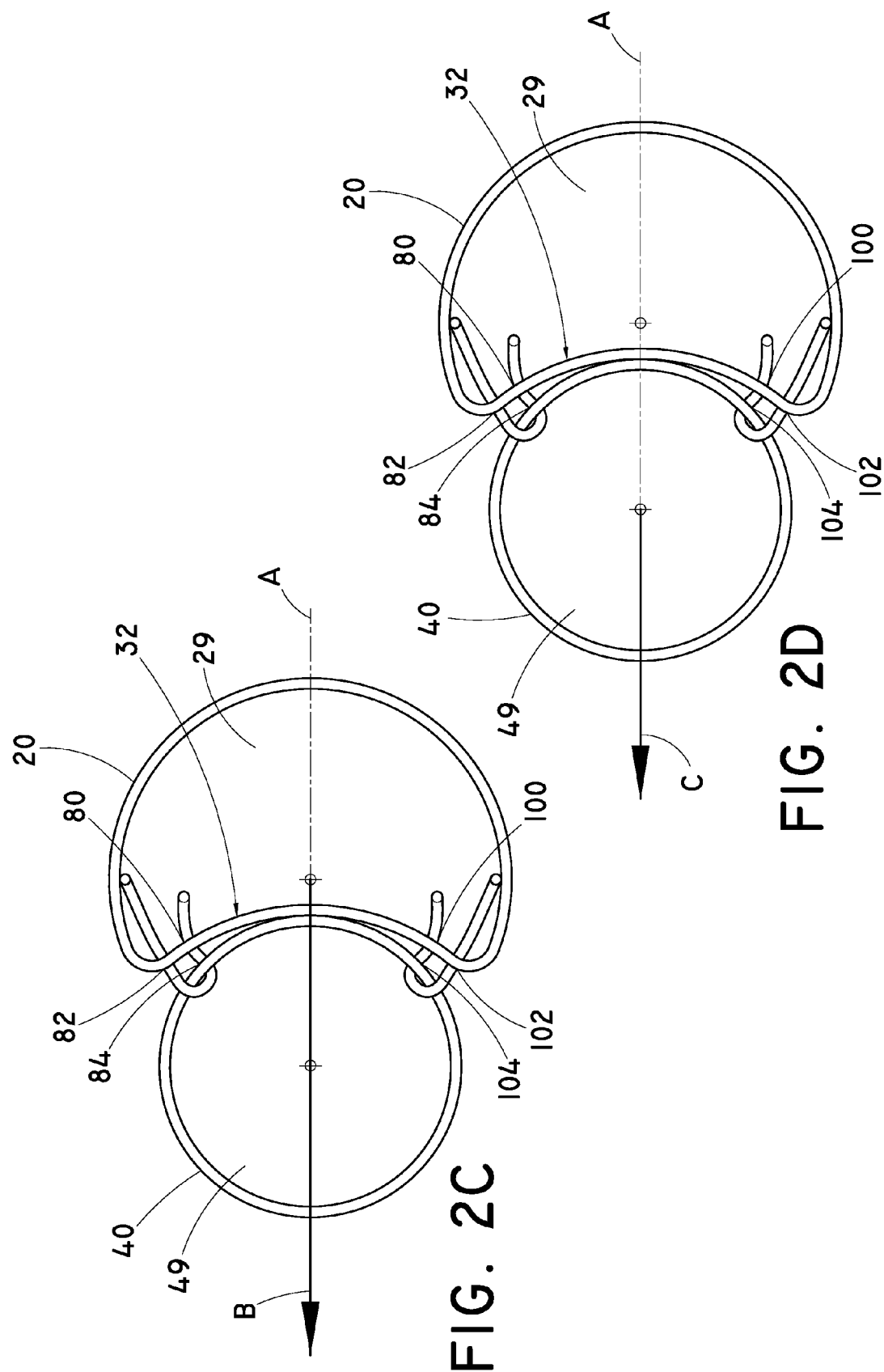

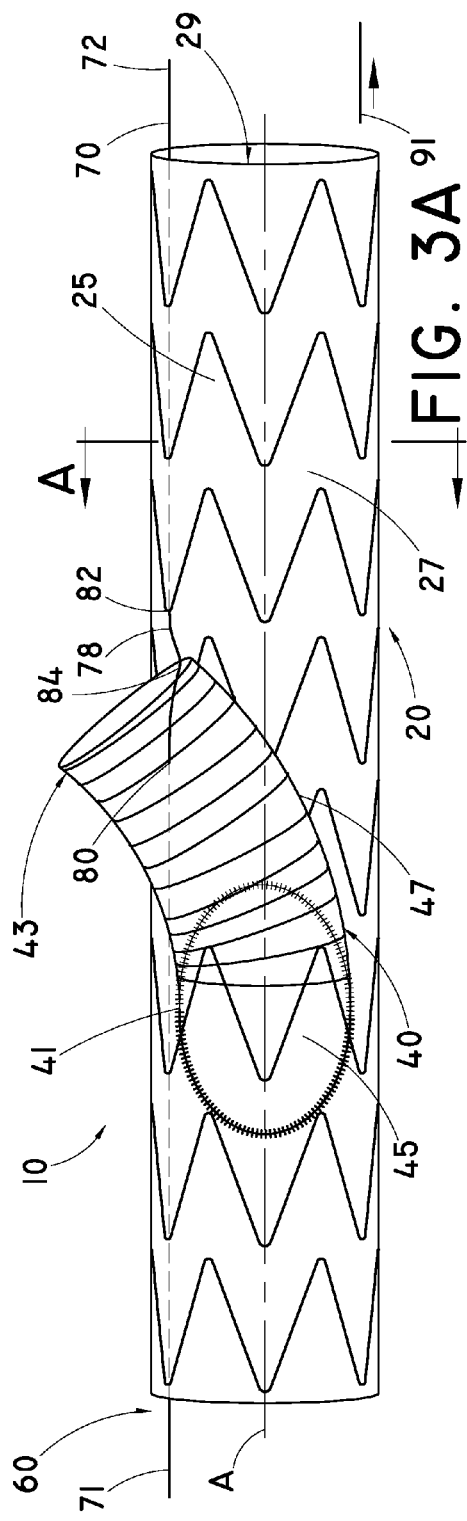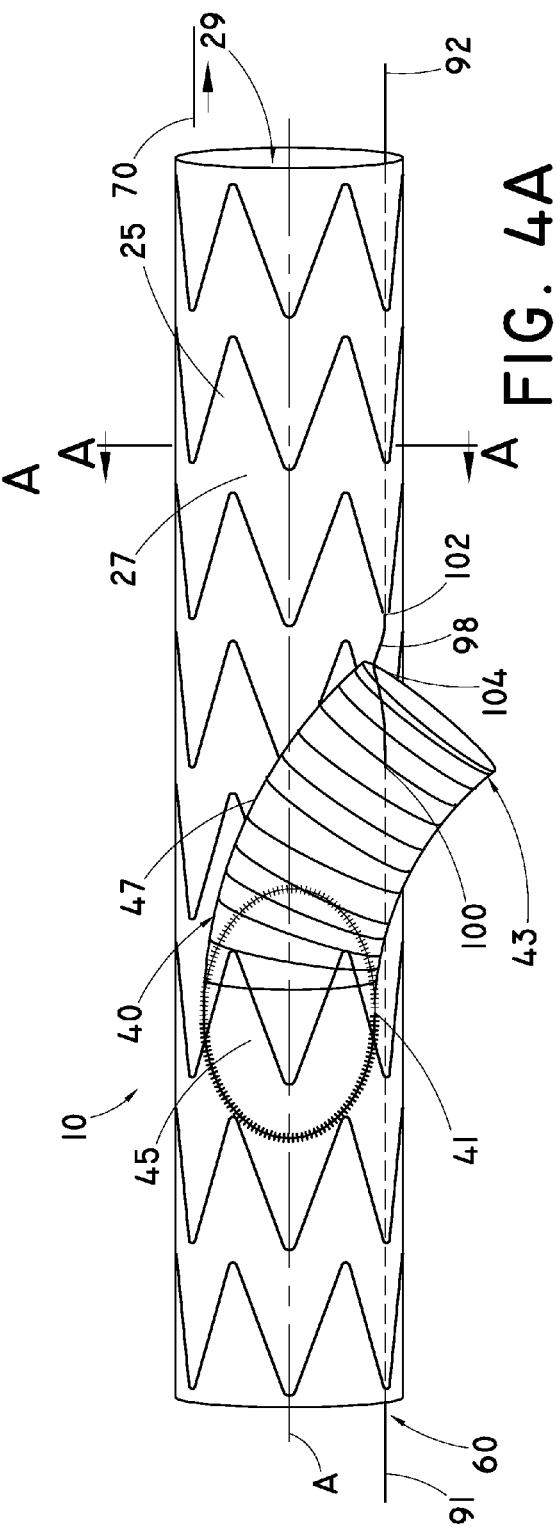

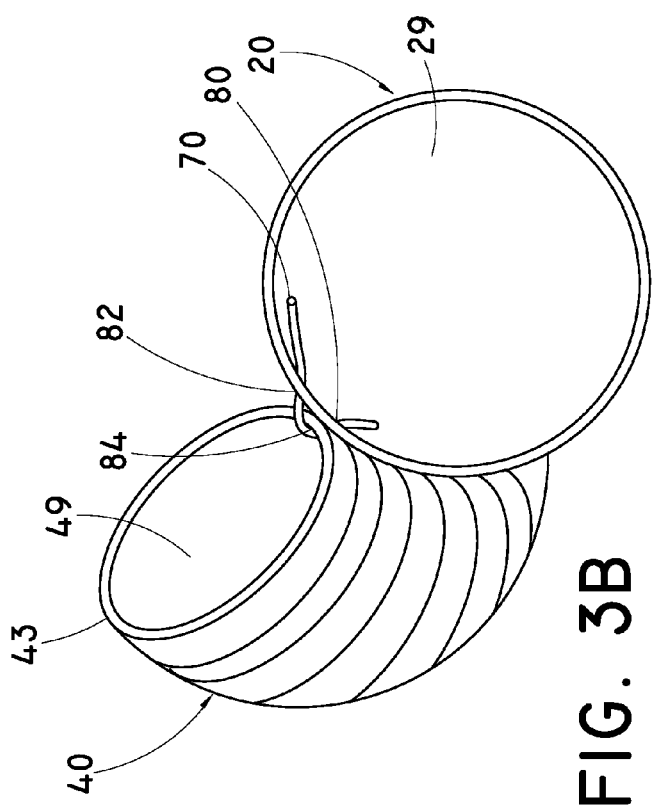
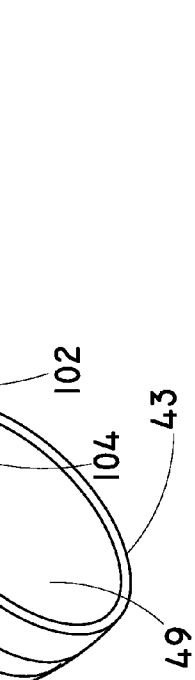

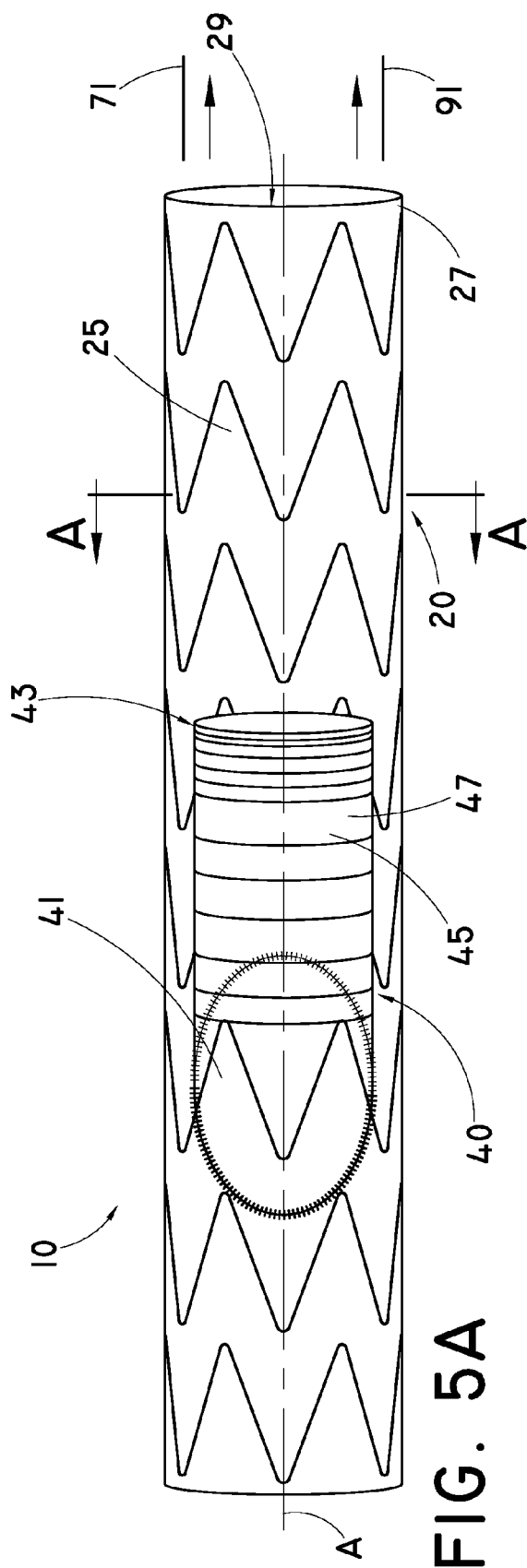
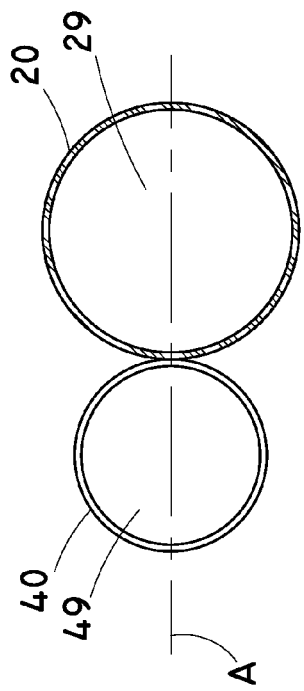
FIG. 5A
FIG. 5B

STEERABLE ILIAC BRANCH DEVICE

CROSS-REFERENCE TO RELATED APPLICATION

This application claims priority and the benefit of provisional U.S. Patent Application Ser. No. 61/485,813, filed May 13, 2011, which is incorporated herein by reference in its entirety.

BACKGROUND

The present disclosure relates generally to medical devices. More particularly, it relates to iliac branch devices for excluding abdominal aortic aneurysms to maintain perfusion of internal iliac arteries.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal, or ruptured vessels involves the use of an endoluminal prosthesis such as a stent graft. Such a prosthesis may provide some or all of the functionality of the original, healthy vessel and/or preserve any remaining vascular integrity by replacing a length of the existing vessel wall that spans the site of vessel failure. It is preferable for the prosthesis to seal off the failed portion of the vessel. For weakened or aneurysmal vessels, even a small leak in the prosthesis may lead to the pressurization of or flow in the treated vessel which may aggravate the condition that the prosthesis was intended to treat. A prosthesis of this type can treat, for example, aneurysms of the abdominal aortic, iliac, or renal arteries. For instance, a prosthesis may be used to span an aneurysm which has occurred in or associated with an iliac artery.

In many cases, such a damaged or defective portion of the vasculature may include a branch vessel. For example, the celiac, superior mesenteric, left common carotid, and renal arteries are branch vessels of the aorta, and the internal iliac artery is a branch vessel of the common iliac artery. If the branch vessel is blocked by the prosthesis, the original blood circulation is impeded, and the patient can suffer. If, for example, the celiac artery is blocked by the prosthesis, the patient can experience abdominal pain, weight loss, nausea, bloating, and loose stools associated with mesenteric ischemia. The blockage of any branch vessel is usually associated with unpleasant or even life-threatening symptoms. Hence, it has been proposed to provide a prosthesis having a side branch which, when deployed, is positioned over the opening to a branch vessel. For example, the iliac branch of a bifurcated aortic prosthesis can be designed to extend into and/or provide flow to the corresponding internal iliac artery. Such a prosthesis is commonly referred to as an iliac branch device (IBD).

Furthermore, an aneurysm may extend into the branch vessel. For example, the aneurysm can progress distally from the aorta through the iliac bifurcation and into the common iliac arteries. The aneurysm may progress a sufficient distance to include one or both internal iliac arteries. An aneurysm including one internal iliac artery is known as a unilateral iliac aneurysm, and an aneurysm including both internal iliac arteries is known as a bilateral iliac aneurysm. Deploying a prosthesis into the branch vessel may help to prevent expansion and/or rupture of such an aneurysm. Another prosthesis such as, for example, a stent graft also can be deployed through the side branch and into the branch vessel to treat the aneurysm extending into the branch vessel and/or provide a blood flow path to the branch vessel.

To accommodate the anatomy of a patient and/or the preference of a physician, the side branch of such a prosthesis typically is biased either to the left or the right side of the body of the prosthesis. For example, an IBD designed to be positioned within one common iliac artery may have a side branch biased to the left and another IBD designed to be positioned in the other common iliac artery may have a side branch biased to the right. Because such IBDs may be mirror images of one another, the two IBDs may not be interchangeable with one another. In other words, each IBD may be suitable for placement only in the common iliac artery for which it was designed, and not in the other common iliac artery.

SUMMARY

An endoluminal prosthesis may be used for treatment of an aneurysmal body vessel.

In one example, an endoluminal prosthesis may include a prosthetic trunk and a prosthetic branch. The prosthetic trunk may include a tubular graft body, an open first end, an open second end, and a trunk lumen in fluid communication with the first end and the second end of the prosthetic trunk. The prosthetic branch may include a tubular graft body, an open first end, an open second end, and a branch lumen in fluid communication with the first end and the second end of the prosthetic branch. The first end of the prosthetic branch may be joined to an intermediate portion of the prosthetic trunk such that the branch lumen is in fluid communication with the trunk lumen. The prosthetic branch may extend from the prosthetic trunk and may be movable with respect to the prosthetic trunk between neutral, right biased, and left biased configurations. In the neutral configuration, the prosthetic branch may be substantially aligned with the prosthetic trunk. In the first biased configuration, the prosthetic branch may extend away from the prosthetic trunk in a first direction to a first side of the prosthetic trunk. In the second biased configuration, the prosthetic branch may extend away from the prosthetic trunk in a second direction to a second side of the prosthetic trunk opposite the first side. The prosthesis may include first releasable steering member associated with the first biased configuration and a second releasable steering member associated with the second biased configuration. The steering members may cooperatively retain the prosthetic branch in the neutral configuration. Upon release of one of the first steering member or the second steering member from the prosthetic branch, the prosthetic branch may move into one of the first biased configuration or the second biased configuration.

In another example, an endoluminal prosthesis may include a prosthetic trunk and a prosthetic branch. The prosthetic trunk may include a tubular graft body, an open first end, an open second end, and a trunk lumen extending between the first end and the second end of the prosthetic trunk. The prosthetic branch may include a tubular graft body, an open first end, an open second end, and a branch lumen extending between the first end and the second end of the prosthetic branch. The first end of the prosthetic branch may be joined to the prosthetic trunk. The branch lumen may be in fluid communication with the trunk lumen. The prosthetic branch may extend outward from the prosthetic trunk. The prosthesis may include a first releasable steering member releasably attached to the second end of the prosthetic branch at a first circumferential position and to the prosthetic trunk at a second circumferential position on a first side of the prosthetic trunk. The prosthesis may include a second releasable steering member releasably attached to the second end of the prosthetic branch at a third circumferential position and to the prosthetic trunk at a fourth circumferential position on a second side of the prosthetic trunk opposite the first side. The first releasable steering member and the second releasable steering member may cooperatively maintain the prosthetic branch in a neutral configuration in which the prosthetic branch is substantially aligned with the prosthetic trunk.

In another example, a method of steering a prosthetic branch between a neutral configuration and one of a first biased configuration or a second biased configuration may include providing a prosthesis including a prosthetic trunk and a prosthetic branch. A first end of the prosthetic branch may be attached to the prosthetic trunk. A second end of the prosthetic branch may be releasably attached to the prosthetic trunk by first and second steering members. The method may include selectively releasing one of the first or second steering members from the prosthetic branch or the prosthetic trunk to enable the prosthetic branch to move to the second biased configuration or the first biased configuration, respectively.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIGS. 2A-2B are schematic views of the prosthesis of FIG. 1 with the prosthetic branch in the neutral configuration.

FIGS. 2C-2D are cross sectional views of the prosthesis of FIGS. 2a-2b.

FIG. 3A is a schematic view of the prosthesis of FIG. 1 with the prosthetic branch in the right biased configuration.

FIG. 3B is a cross sectional view of the prosthesis of FIG. 3a.

FIG. 4A is a schematic view of the prosthesis of FIG. 1 with the prosthetic branch in the left biased configuration.

FIG. 4B is a cross sectional view of the prosthesis of FIG. 4a.

FIG. 5A is a schematic view of the prosthesis of FIG. 1 with the prosthetic branch in the free configuration.

FIG. 5B is a cross sectional view of the prosthesis of FIG. 5a.

DETAILED DESCRIPTION OF THE DRAWINGS AND THE PRESENTLY PREFERRED EMBODIMENTS

Throughout this disclosure, the term "distal" is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

Figure 1:
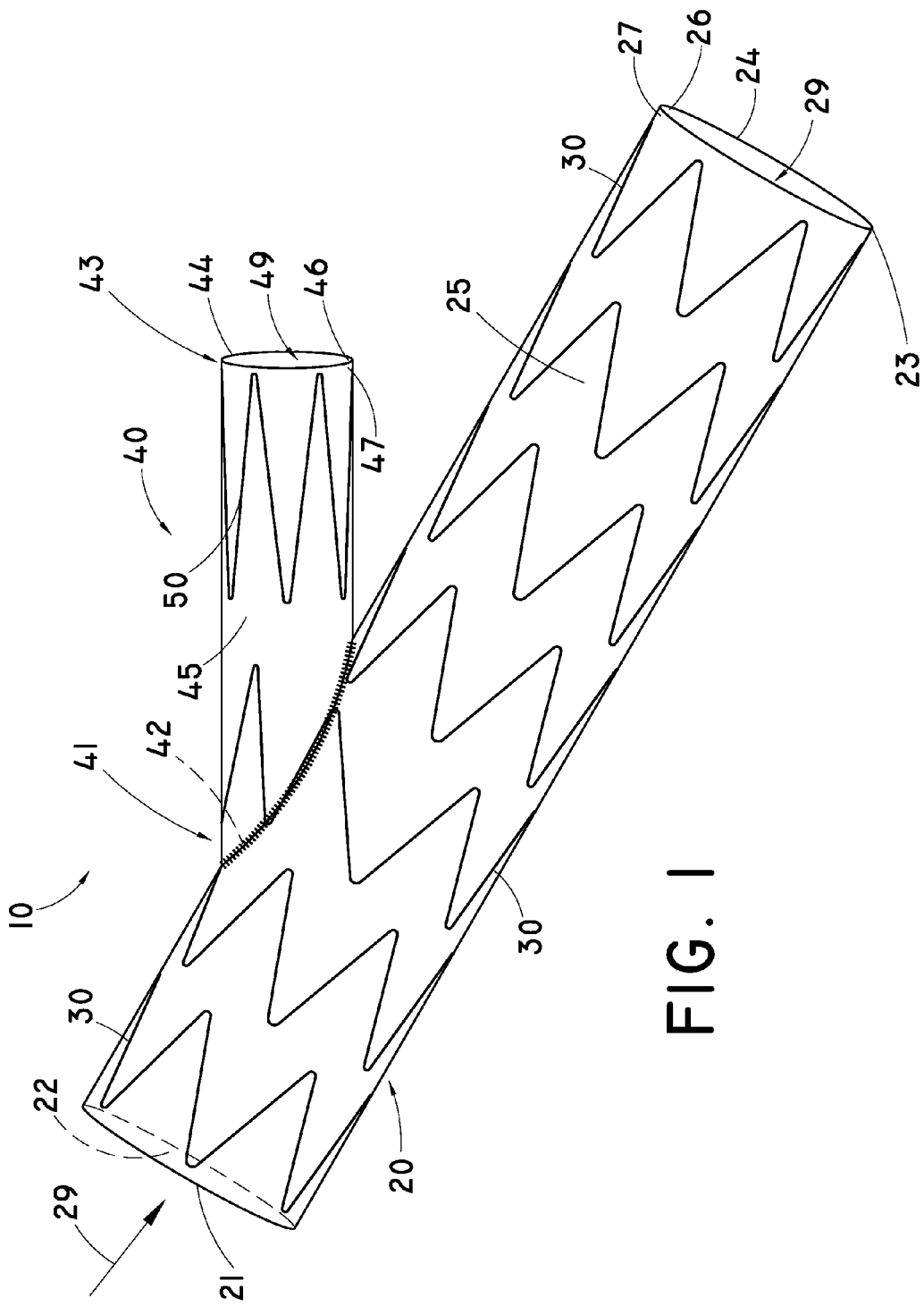
FIG. 1 depicts one example of a prosthesis having a prosthetic trunk and a prosthetic branch.

FIG. 1 depicts one embodiment of a prosthesis 10 having a prosthetic trunk 20 and a prosthetic branch 40. The prosthetic trunk 20 has a first end 21 with a first end opening 22 and a second end 23 with a second end opening 24. The prosthetic trunk 20 can include a substantially tubular graft body 25 having an inner surface 26 and an outer surface 27. The graft body 25 may form a generally cylindrical configuration. The inner surface 26 of the graft body 25 can define a trunk lumen 29 extending longitudinally between the first end 21 and the second end 23 of the prosthetic trunk 20. The trunk lumen 29 may be suitable for passing fluid therethrough. The prosthetic trunk 20 further can include at least one support structure 30, such as a stent. The support structure 30 may include a single, unitary structure or a plurality of independent structures. The support structure 30 and/or various portions thereof may be disposed on the inner surface 26 and/or the outer surface 27 of the graft body 25. Multiple support structures 30 may be positioned at any points along a length of the prosthetic trunk 20.

The prosthetic branch 40 has a first end 41 with a first end opening 42 and a second end 43 with a second end opening 44. The prosthetic branch 40 can include a substantially tubular graft body 45 having an inner surface 46 and an outer surface 47. The graft body 45 may form a generally cylindrical configuration. The inner surface 46 of the graft body 45 can define a branch lumen 49 extending longitudinally between the first end 41 and the second end 43 of the prosthetic branch 40. The branch lumen 49 may be suitable for passing fluid therethrough. The prosthetic branch 40 further can include at least one support structure 50. The support structure 50 may include a single, unitary structure or a plurality of independent structures. The support structure 50 and/or various portions thereof may be disposed on the inner surface 46 and/or the outer surface 47 of the graft body 45. Multiple support structures 50 may be positioned at any points along a length of the prosthetic branch 40.

The first end 41 of the prosthetic branch 40 may be attached to the prosthetic trunk 20 so that the prosthetic branch may extend from the graft body 25 of the prosthetic trunk. The prosthetic branch 40 may extend from the prosthetic trunk 20 such that the prosthesis 10 may have a generally Y shaped configuration as shown in FIG. 1. The prosthetic branch 40 may be configured as a peripheral branch extending from a side of the prosthetic trunk 40 or a contralateral branch attached to a leg of a Y formed by the prosthetic trunk. The prosthetic branch 40 may extend from the prosthetic trunk 20 at any angle with respect to the body 25 of the prosthetic trunk. Preferably, the prosthetic branch 40 may extend from the prosthetic trunk 20 at an acute angle as shown in FIG. 1. The prosthetic branch 40 may be attached to the prosthetic trunk 20 at any point along a length of the prosthetic trunk extending between the first end 21 and the second end 23 of the prosthetic trunk. For example, the first end 41 of the prosthetic branch 40 may be attached to the prosthetic trunk 20 at an intermediate portion of the prosthetic trunk as shown in FIG. 1. Preferably, the prosthetic branch 40 may be attached to the prosthetic trunk 20 at a position that enables portions of the prosthetic trunk proximal and distal of the prosthetic branch to engage a wall of a body vessel and/or another prosthesis for treatment of an aneurysm.

The prosthetic branch 40 may be attached to the prosthetic trunk 20 by sutures, wire, staples, clips, bonding agents, or other methods that may be used to achieve a secure attachment. For example, the prosthetic branch 40 may be attached to the prosthetic trunk 20 by any method described in U.S.

Patent Application Pub. No. 2006/0095118 by Hartley which is incorporated by reference herein in its entirety. The prosthetic branch 40 may be attached to the graft body 25 and/or the support structure 30 of the prosthetic trunk. Preferably, the graft body 45 of the prosthetic branch 40 may be attached to the graft body 25 of the prosthetic trunk 20 to form a fluid-tight seal. For example, the graft body 45 of the prosthetic branch 40 may be stitched to the graft body 25 of the prosthetic trunk 20. An aperture may be formed in the graft body 25 of the prosthetic trunk 20. The aperture may be aligned with the first end opening 42 of the prosthetic branch 40 to enable fluid communication between the trunk lumen 29 and the branch lumen 49 through the aperture. In this manner, the prosthesis 10 may be configured to serve as a conduit for blood to flow through the trunk and branch lumens 29, 49 between the first end 21 of the prosthetic trunk 20 and the second ends 23, 43 of the prosthetic trunk and the prosthetic branch 40, respectively.

The second end 43 of the prosthetic branch 40 may be movable with respect to the prosthetic trunk 20 as further described herein. To that end, the prosthetic branch 40 may be sufficiently flexible to enable the second end 43 of the prosthetic branch to be moved, for example, into abutting contact with the graft body 25 of the prosthetic trunk. Such flexibility further may enable the prosthetic branch to move from a neutral configuration to various biased configurations (e.g., a right or left biased configuration) as further described herein. The graft body 45 of the prosthetic branch 40 may be crimped to increase flexibility and/or decrease the risk of kinking, thereby helping to preserve the patency of the prosthetic branch. Suitable crimps and methods for crimping the prosthetic branch are described in U.S. Pat. No. 7,407,509 to Greenberg et al. and U.S. Patent Application Pub. No. 2005/0113905 by Greenberg et al., which are incorporated by reference herein in their entirety.

The prosthesis 10 may be sized and shaped for placement within the vasculature of a patient for treatment of an aneurysmal body vessel. The preferred size and shape of the prosthesis 10 depend on the anatomy in which it is to be implanted. Physiological variables, deployment characteristics, and other factors also may contribute to the determination of a proper size and shape of the prosthesis 10. For example, the prosthesis 10 may have a size and shape suitable for placement at a common iliac bifurcation. To that end, the prosthetic trunk 20 may be configured for placement within a common iliac artery, and the prosthetic branch 40 may be configured to extend from the common iliac artery into an internal iliac artery. The prosthetic trunk 20 may have a diameter, for example, ranging from about 10 mm to about 36 mm, typically from about 22 mm to about 36 mm. The diameter of the prosthetic trunk 20 may be constant along the length of the prosthetic trunk. Alternatively, the prosthetic trunk 20 may be tapered such that the diameter of the prosthetic trunk may vary along the length of the prosthetic trunk. The prosthetic branch 40 may have a diameter, for example, ranging from about 6 mm to about 24 mm, typically from about 8 mm to about 12 mm. The diameter of the prosthetic branch 40 may be constant along the length of the prosthetic branch. Alternatively, the prosthetic branch 40 may be tapered such that the diameter of the prosthetic branch may vary along the length of the prosthetic branch. The prosthesis 10 may be deployed in combination with various other prostheses to effectively bridge an aneurysmal portion of the vasculature.

It is further contemplated that a prosthesis may have multiple prosthetic branches extending from a prosthetic trunk. For example, the prosthesis may have two, three, or more prosthetic branches extending from the prosthetic trunk. The various branches may be attached to the prosthetic trunk at varying longitudinal and/or circumferential positions with respect to the prosthetic trunk. In this manner, the prosthesis may be configured for placement at various positions within the vasculature of the patient.

The graft bodies 25, 45 may be made of any material known in the art. For example, the graft bodies may be made of an expanded polytetrafluoroethylene (ePTFE), polytetrafluoroethylene, silicone, polyurethane, polyamide (nylon), as well as other flexible biocompatible materials. The graft bodies also can be made of known fabric graft materials such as woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). The graft bodies also may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, and uterine submucosa. One non-limiting example of a suitable remodelable material is SURGISIS® BIODESIGN™ from Cook Medical (Bloomington, Ind.). Another suitable remodelable material is the graft prosthesis material described in U.S. Pat. No. 6,206,931 to Cook et al., which is incorporated herein by reference in its entirety. The graft bodies also may be made of any of the materials described in U.S. Pat. No. 7,407,509 to Greenberg et al. or U.S. Patent Application Pub. No. 2009/0171451 by Kuppurathanam et al., which are incorporated herein by reference in their entirety.

The support structures 30, 50 and/or various portions thereof can be stents having any suitable stent pattern known in the art. The stents may be balloon expandable. Preferably, the stents may be self-expandable. The stents can maintain the patency of the prosthesis and ensure adequate sealing against the surrounding vascular tissue. One goal for stent design and placement, whether internal or external, may be to prevent metal-to-metal contact points, prevent contact between two different types of alloys, and minimize micromotion. Stent sizing, spacing, and design may be determined so that there is no stent-to-stent contact even in tortuous anatomy. Stents preferably may be placed to maximize prosthesis flexibility while maintaining patency, as well as reduce material wear and stent fatigue. Furthermore, it is preferable that the stents do not interfere with the prosthetic branch, that they minimize the potential for galvanic corrosion, and ensure adequate joint stability. Stent amplitude, spacing, and stagger preferably may be optimized for each prosthesis design. Any of the stents mentioned herein may have barbs and/or other anchoring members to help decrease prosthesis migration.

One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. The Z-stent design may be preferred for straight sections of the aorta. It provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents have the potential to become intertwined with the wires and other devices utilized to ensure branch vessel access, sealing, and fixation. Thus, in some instances, it may be desirable to affix some of the stents to the internal surface of the prosthesis. The stents mentioned herein may be made from standard medical grade stainless steel and soldered using silver standard solder (0 lead/0 tin). Other stents may be made from nitinol or other shape-memory metal.

The prosthetic branch 40 of the prosthesis 10 may be steerable between a neutral configuration and various biased configurations with respect to the prosthetic trunk 20 as shown in FIGS. 2a-4b. FIGS. 2a-2d depict the prosthesis 10 with the prosthetic branch 40 in the neutral configuration. In the neutral configuration, the prosthetic branch 40 may be disposed generally longitudinally along the prosthetic trunk 20. In other words, the prosthetic branch 40 may extend from the prosthetic trunk 20 in a direction that is generally parallel to the longitudinal axis of the prosthetic trunk. The outer surface 47 of the graft body 45 of the prosthetic branch 40 may be in abutting contact with the outer surface 27 of the graft body 25 of the prosthetic trunk 20, and the longitudinal axis of the prosthetic branch may be substantially coplanar with the longitudinal axis of the prosthetic trunk. The prosthetic branch 40 may be generally aligned with the prosthetic trunk 20 such that the outer surface 47 of the graft body 45 of the prosthetic branch may be in abutting contact with the outer surface 27 of the graft body 25 of the prosthetic trunk along substantially an entire length of the prosthetic branch extending between the first and second ends 41, 43 thereof. The second end 43 of the prosthetic branch 40 may be releasably attached to the prosthetic trunk 20 at multiple points along the circumference of the prosthetic branch to retain the prosthetic branch in the neutral configuration as further described herein. The prosthetic branch may be movable from the neutral configuration to a biased configuration by selectively releasing the prosthetic branch retained in the neutral configuration from one of the multiple points of attachment to the prosthetic trunk as further described herein.

FIGS. 3a-3b depict the prosthesis 10 with the prosthetic branch 40 in a first, right biased configuration. In the right biased configuration, the prosthetic branch 40 may be disposed longitudinally and transversely along the prosthetic trunk 20. In other words, the prosthetic branch 40 may extend from the prosthetic trunk 20 in a direction having a longitudinal component that is parallel to the longitudinal axis of the prosthetic trunk and a transverse component that is perpendicular to and away from the longitudinal axis of the prosthetic trunk. The prosthetic branch 40 also may extend circumferentially about the prosthetic trunk 20. In other words, the prosthetic branch 40 may extend from the prosthetic trunk 20 in a direction having an angular component about the longitudinal axis of the prosthetic trunk. At least a portion of the outer surface 47 of the graft body 45 of the prosthetic branch 40 may be in abutting contact with the outer surface 27 of the graft body 25 of the prosthetic trunk 20. The prosthetic branch 40 may be curved such that the longitudinal axis of the prosthetic branch may not be linear. FIGS. 4a-4b depict the prosthesis 10 with the prosthetic branch 40 in a second, left biased configuration. The position of the prosthetic branch 40 in the left biased configuration may be a mirror image of the position of the prosthetic branch in the right biased configuration. The second end 43 of the prosthetic branch 40 may be releasably attached to the prosthetic trunk 20 at a single point along the circumference of the prosthetic branch to retain the prosthetic branch in one of the right biased configuration and the left biased configuration as further described herein.

The prosthetic branch 40 may be steerable between the neutral, right biased, and/or left biased configurations using a steering system 60. The steering system 60 may include at least one generally filamentary steering member. For example, the steering system 60 may include a first, right steering member 70 and a second, left steering member 90 as shown in FIGS. 2a-2d. The steering members may be releasably attached to the prosthetic trunk 20 and the prosthetic branch 40 to releasably attach the second end 43 of the prosthetic branch to the prosthetic trunk. The configuration of the prosthetic branch 40 with respect to the prosthetic trunk 20 may be adjusted by selective release of the right and/or left steering members as further described herein.

FIGS. 2a-2d depict the prosthesis 10 with the prosthetic branch 40 in the neutral configuration. In the neutral configuration, the longitudinal axis of the prosthetic branch 40 and the longitudinal axis of the prosthetic trunk 20 may be substantially coplanar along a plane A. A ray B may extend from the longitudinal axis of the prosthetic trunk 20 along the plane A as shown in FIG. 2c. The longitudinal axis of the prosthetic trunk 20 and the ray B may form a reference axis and a reference direction of a first cylindrical coordinate system of the prosthetic trunk. The position of any point along the body 25 of the prosthetic trunk 20 may have a longitudinal component with respect to the longitudinal axis of the prosthetic trunk and an angular component with respect to the ray B. Likewise, a ray C may extend from the longitudinal axis of the prosthetic branch as shown in FIG. 2d. The ray C may extend in substantially the same direction as the ray B. The longitudinal axis of the prosthetic branch 40 and the ray C may form a reference axis and a reference direction of a second cylindrical coordinate system of the prosthetic branch. The position of any point along the body 45 of the prosthetic branch 40 may have a longitudinal component with respect to the longitudinal axis of the prosthetic branch and an angular component with respect to the ray C.

The second end 43 of the prosthetic branch 40 may be releasably attached to the prosthetic trunk 20 to retain the prosthetic branch in one of the neutral configuration, the right biased configuration, and the left biased configuration. The second end 43 of the prosthetic branch 40 may be releasably attached to the prosthetic trunk 20 by any means. For example, the second end 43 of the prosthetic branch 40 may be releasably attached to the prosthetic trunk 20 by pullable sutures or threads. The sutures or threads may be configured to be released by, for example, severing the sutures or threads or manipulating a trigger wire. In the example shown in FIGS. 2a-2d, the second end 43 of the prosthetic branch 40 may be releasably attached to the prosthetic trunk 20 by the right and left steering members 70, 90. The steering members may be threaded through the prosthetic trunk 20 and/or the prosthetic branch 40 as described herein to releasably attach the second end 43 of the prosthetic branch to the prosthetic trunk.

The right steering member 70 may have a first end 71 and a second end 72. At least a portion of the right steering member 70 may be disposed generally longitudinally within the trunk lumen 29 of the prosthetic trunk 20 as shown in FIG. 2a. The right steering member may be threaded through the graft bodies of the prosthetic trunk 20 and/or the prosthetic branch 40. For example, the right steering member 70 may penetrate the graft body 25 of the prosthetic trunk 20 at a first penetration point 80. The right steering member 70 also may penetrate the graft body 25 of the prosthetic trunk 20 at a second penetration point 82. A segment 78 of the right steering member 70 extending between the first and second penetration points 80, 82 may be disposed external to the prosthetic trunk 20. The first penetration point 80 may have a longitudinal position proximal to the second end 43 of the prosthetic branch 40. The first penetration point 80 may be positioned at any point along the circumference of the prosthetic trunk 20. Preferably, the first penetration point 80 may be positioned angularly away from the plane A. For example, the first penetration point 80 may have an angular position that is about 270 degrees from the ray B as shown in FIG. 2c. The second penetration point 82 may have a longitudinal position distal to the second end 43 of the prosthetic branch 40. The second penetration point 82 may be positioned at any point along the circumference of the prosthetic trunk 20. Preferably, the second penetration point 80 may be positioned angularly away from the plane A. The angular position of the second penetration point 82 may be the same as or different than the angular position of the first penetration point 80. For example, the second penetration point 82 may have an angular position that is about 270 degrees from the ray B as shown in FIG. 2c. In other words, the first and second penetration points 80, 82 may be positioned at the same angular position, and the second penetration point may have a longitudinal position distal to the longitudinal position of the first penetration point. In one example, the first and second penetration points 80, 82 may be spaced longitudinally from one another by about 4 mm to about 8 mm.

The external segment 78 of the right steering member 70 may include a curve or a bend as shown in FIGS. 2a-2d. Such a curve or bend may be configured to migrate along the right steering member 70 as the right steering member moves relative to the prosthetic trunk 20 and/or the prosthetic branch 40 as further described herein. In other words, the right steering member 70 may be sufficiently flexible that the curve or bend in the external segment 78 may form and/or deform upon movement of the right steering member relative to the prosthetic trunk 20 and/or the prosthetic branch 40. The external segment 78 may be releasably attached to the second end 43 of the prosthetic branch 40. To this end, the external segment 78 may be configured to at least partially encircle an annular portion of the prosthetic branch 40 proximate the second end 43 thereof. For example, the external segment 78 of the right steering member 70 may penetrate the graft body 45 of the prosthetic branch 40 at a third penetration point 84. The third penetration point 84 may have a longitudinal position proximate the second end 43 of the prosthetic branch 40. In one example, the third penetration point 84 may be spaced from the second end opening 44 of the prosthetic branch 40 by a longitudinal distance of about 2 mm to about 6 mm. Preferably, the third penetration point 84 may have a longitudinal position that is between the longitudinal positions of the first and second penetration points 80, 82, respectively. The third penetration point 84 may be positioned at any point along the circumference of the prosthetic branch 40. Preferably, the third penetration point 84 may be positioned angularly away from the plane A. For example, the third penetration point 84 may have an angular position that is about 270 degrees from the ray C as shown in FIG. 2d. The external segment 78 of the right steering member 70 further may pass through the second end opening 44 of the prosthetic branch 40 to at least partially encircle an annular portion of the prosthetic branch extending longitudinally between the third penetration point 84 and the end opening 44 of the prosthetic branch. In this manner, the second end 43 of the prosthetic branch 40 may be retained by the external segment 78 of the right steering member between the first and second penetration points 80, 82.

Likewise, the left steering member 90 may have first and second ends 91, 92. The left steering member 90 may penetrate the graft body 25 of the prosthetic trunk 20 at fourth and fifth penetration points 100, 102. A segment 98 of the left steering member 90 extending between the fourth and fifth penetration points 100, 102 may be disposed external to the prosthetic trunk 20. The fourth penetration point 100 may have a longitudinal position proximal to the second end 43 of the prosthetic branch 40. For example, the fourth penetration point 100 may have a longitudinal position that is the same as the longitudinal position of the first penetration point 80. The fourth penetration point 100 may be positioned at any point along the circumference of the prosthetic trunk 20. The first and fourth penetration points 80, 100 may be positioned about 180 degrees apart from one another with respect to a circumference of the prosthetic trunk 20. For example, the fourth penetration point 100 may have an angular position that is about 90 degrees from the ray B as shown in FIG. 2c. The fifth penetration point 102 may have a longitudinal position distal to the second end 43 of the prosthetic branch 40. For example, the fifth penetration point 102 may have a longitudinal position that is the same as the longitudinal position of the second penetration point 82. The fifth penetration point 102 may be positioned at any point along the circumference of the prosthetic trunk 20. The angular position of the fifth penetration point 102 may be the same as or different than the angular position of the fourth penetration point 100. For example, the fifth penetration point 102 may have an angular position that is about 90 degrees from the ray B as shown in FIG. 2c. In other words, the fourth and fifth penetration points 100, 102 may be positioned at the same angular position, and the fifth penetration point may have a longitudinal position distal to the longitudinal position of the fourth penetration point.

Like the external segment 78 of the right steering member 70, the external segment 98 of the left steering member 90 may include a curve or a bend as shown in FIGS. 2a-2d. The external segment 98 may be releasably attached to the second end 43 of the prosthetic branch 40. For example, the external segment 98 of the left steering member 90 may penetrate the graft body 45 of the prosthetic branch 40 at a sixth penetration point 104. The sixth penetration point 104 may have a longitudinal position proximate the second end 43 of the prosthetic branch 40. For example, the sixth penetration point 104 may have a longitudinal position that is the same as the longitudinal position of the third penetration point 84. The sixth penetration point 104 may be positioned at any point along the circumference of the prosthetic branch 40. The sixth penetration point 104 may be positioned such that the third and sixth penetration points 84, 104 may be spaced the same angular distance from the plane A and on opposite sides of the plane A from one another. For example, the sixth penetration point 104 may have an angular position that is about 90 degrees from the ray C as shown in FIG. 2d. The external segment 98 of the left steering member 90 further may pass through the second end opening 44 of the prosthetic branch 40 to at least partially encircle an annular portion of the prosthetic branch extending longitudinally between the sixth penetration point 104 and the end opening 44 of the prosthetic branch. In this manner, the second end 43 of the prosthetic branch 40 may be retained by the external segment 98 of the left steering member between the fourth and fifth penetration points 100, 102.

The steering members may be any type of filamentary members known in the art. Preferably, the steering members may be made of a material that exhibits sufficient flexibility to be threaded through the prosthesis and sufficient stiffness to be manipulated to steer the prosthetic branch as described herein. The steering members may be made of, for example, biocompatible metals including, but not limited to, nitinol and stainless steel. For further example, the steering members also may be made of suture materials including, but not limited to, polylactic acid, polyglycolic acid, polydioxane, nylon, polypropylene, or any suitable biocompatible biomaterial such as VICRYL® from Ethicon, Inc. (Somerville, N.J.).

Other means and/or configurations for releasably attaching the steering members to the prosthetic trunk and/or the prosthetic branch are further contemplated within the scope of this disclosure. For example, the steering members may extend generally longitudinally along the outer surface of the prosthetic trunk. For further example, the steering members may extend within a sleeve that may be attached to the inner surface or the outer surface of the prosthetic trunk. The steering members also may be threaded through the graft bodies of the prosthetic trunk and/or the prosthetic branch in any manner and/or may penetrate the graft bodies any number of times through any number of penetration points.

The various penetration points described herein may be configured as any type of penetration through the graft body of the prosthetic trunk and/or the prosthetic branch. For example, the penetration points may be configured as holes or slits in the graft material of the graft body. Preferably, the penetration points may be configured to have self-sealing properties. In other words, the penetration points may be configured to reduce leakage of blood and/or other body fluids therethrough. The penetration points may or may not be reinforced by, for example, grommets. In one example, the penetration points may be configured as reinforced holes such as those described in U.S. Patent Application Pub. No. 2009/0149939 by Godlewski et al., which is incorporated by reference herein in its entirety.

In the neutral configuration, at least a portion of the second end 43 of the prosthetic branch 40 may be receivably engaged by a recess 32 formed in the graft body 25 of the prosthetic trunk 20 as shown in FIGS. 2b-2d. A portion of the prosthetic trunk 20 that may include the recess 32 may have a generally crescent shaped cross section, as shown in FIGS. 2c-2d, with the recess forming the concave portion of the crescent. The recess 32 may be formed by the second end 43 of the prosthetic branch 40 being drawn radially inward toward the longitudinal axis of the prosthetic trunk 20. In other words, the second end 43 of the prosthetic branch 40 may be drawn inward to deform the graft body 25 of the prosthetic trunk 20 to form the recess 32. The second end 43 of the prosthetic branch 40 may be drawn radially inward toward the longitudinal axis of the prosthetic trunk 20 by the right and/or left steering members 70, 90. For example, the right steering member 70 may be slidably received within the first, second, and/or third penetration points 80, 82, 84. The first and/or second ends 71, 72 of the right steering member 70 may be pulled taught to cause the right steering member to slide within the first, second, and/or third penetration points such that the first and second ends 71, 72 may move in opposite longitudinal directions relative to one another. Such movement may cause a portion of the external segment 78 of the right steering member 70 to be drawn into the trunk lumen 29 of the prosthetic trunk 20 through the first and/or second penetration points 80, 82. Concurrently, the second end 43 of the prosthetic branch 40 may be drawn radially inward toward the longitudinal axis of the prosthetic trunk 20. In other words, such movement may result in the length of the external segment 78 being reduced to draw the second end 43 of the prosthetic branch 40 radially inward. The second end 43 of the prosthetic branch 40 may be drawn radially inward toward the longitudinal axis of the prosthetic trunk 20 by the left steering member 90 in a similar manner to form the recess 32 in the prosthetic trunk. Formation of the recess 32 may enable the prosthesis 10 to have a smaller outer diameter for more efficient delivery within the vasculature of a patient. The recess 32 further may help to retain the prosthetic branch 40 in the neutral configuration during delivery within the vasculature of the patient. Deformation of the recess 32 may help to urge the prosthetic branch toward the right or left biased configuration as further described herein.

The prosthetic branch 40 may be steerable between the neutral, right biased, and/or left biased configurations using the steering system 60. Selective release of one of the right and left steering members 70, 90 from the prosthetic branch 40 and/or the prosthetic trunk 20 may enable the prosthetic branch to move to the left or right biased configuration, respectively. The steering members may cooperate, for example by providing a counter tension on the prosthetic branch 40, to hold the prosthetic branch in the neutral configuration. For example, the right steering member may exert a force on the prosthetic branch 40 that tends to pull the prosthetic branch to the right (i.e., toward a right side of the prosthetic trunk 20). Conversely, the left steering member 90 may exert a force on the prosthetic branch 40 that tends to pull the prosthetic branch to the left (i.e., toward a left side of the prosthetic trunk 20). The opposing forces exerted by the right and left steering members may result in the prosthetic branch 40 being retained in the neutral configuration. Upon release of one of the steering members, the counter tension may be released. In the absence of a force pulling the prosthetic branch 40 in the opposite direction, the prosthetic branch 40 may bias in the direction of the remaining steering member. In other words, upon release of the left steering member 90, the second end 43 of the prosthetic branch 40 may move to extend in a direction away from the prosthetic trunk 20 and to the right side of the prosthetic trunk. Similarly, upon release of the right steering member 70, the second end 43 of the prosthetic branch 40 may move to extend in a direction away from the prosthetic trunk 20 and to the left side of the prosthetic trunk. The right and left sides of the prosthetic trunk may be positioned on opposite sides of a plane including the longitudinal axis of the prosthetic trunk 20 and passing through the first end 41 of the prosthetic branch (e.g., a plane including the ray B).

For example, the left steering member 90 may be released from the prosthetic branch 40 and/or the prosthetic trunk 20 to enable the prosthetic branch to move to the right biased configuration. The left steering member 90 may be released from the prosthetic branch 40 and/or the prosthetic trunk 20 by, for example, retracting the first end 91 or the second end 92 of the left steering member to unthread the steering member from the prosthetic branch and/or the prosthetic trunk. The left steering member 90 may be slidably received within the fourth, fifth, and/or sixth penetration points 100, 102, 104 such that retraction of the first end 91 or the second end 92 may cause the left steering member to slide within the fourth, fifth, and/or sixth penetration points. The first or second end 91, 92 of the left steering member 90 may be retracted until the first end 91 or the second end 92 may slide out of engagement with the fourth, fifth, and/or sixth penetration points. In other words, an end of the left steering member 90 may be retracted to pull (i.e., unthread) the left steering member out of engagement with the prosthetic trunk 20 and/or the prosthetic branch 40. With the left steering member 90 no longer received within the fourth, fifth, and/or sixth penetration points, the left steering member may release from the prosthetic trunk 20 and/or the prosthetic branch 40 to enable the prosthetic branch to move from the neutral configuration to the right biased configuration as shown in FIGS. 3a-3b.

The right steering member 70 may remain releasably attached to the prosthetic trunk 20 and/or the prosthetic branch 40 after release of the left steering member 90. The second end 43 of the prosthetic branch 40 may be urged radially outward away from the longitudinal axis of the prosthetic trunk 20 by the expansion force of the prosthetic trunk. In other words, the expansion force of the prosthetic trunk may cause the recess 32 to deform and the portion of the prosthetic trunk proximate the second end 43 of the prosthetic branch 20 to expand toward an expanded configuration. The distal end 43 of the prosthetic branch 40 may be urged radially outward away from the longitudinal axis of the prosthetic trunk 20 concurrent with the deformation of the recess 32. At the same time, the second end 43 of the prosthetic branch 40 may be urged rightward by the right steering member 70 which may remain releasably attached thereto to urge the prosthetic branch toward the right biased configuration. Conversely, the right steering member 70 may be released from the prosthetic branch 40 and/or the prosthetic trunk 20 with the left steering member 90 remaining releasably attached to the prosthetic trunk and/or the prosthetic branch to enable the prosthetic branch to move to the left biased configuration of FIGS. 4*a*-4*b* in similar fashion.

In one preferred embodiment, two independent steering trigger wires are utilized. A first wire (i.e., the right steering member) traverses up a delivery system, exits a pusher, and enters the lumen of the main body (i.e., the prosthetic trunk) from the distal end. The first wire pierces the graft at ~3:00 orientation just distal to the distal margin of the branch. The wire then enters the branch from the distal end, progresses ~4 mm proximally in the branch, then pierces it to exit. The wire then pierces the main body to re-enter the lumen, and progresses lumenally and exits the proximal end of the device. A second steering trigger wire (i.e., the left steering member) takes the same path as the first wire, but pierces the main body at ~9:00 orientation. When both wires are in place, the branch is held at 12:00, but when either wire is removed, the branch turns to bias in the direction of the remaining wire. This allows the physician to give the device bias in either direction to best accommodate patient anatomy while minimizing part numbers and stock levels at clinics.

In another embodiment, pullable sutures or threads may be used. For example, the second end of the prosthetic branch may be sutured to the prosthetic trunk to retain the prosthetic branch in the neutral configuration. Multiple sutures may be spaced, for example, about 180 degrees apart from one another around the circumferences of the prosthetic trunk and the prosthetic branch, respectively. The sutures may releasably attach the prosthetic branch to the prosthetic trunk at approximately the same longitudinal and angular positions as the penetration points described herein. The sutures may be released, for example, by manipulating a trigger wire, severing the sutures, or releasing a slip knot. Further for example, the second end of the prosthetic branch may be releasably attached to the prosthetic trunk by clips, wire, staples, bonding agent, or any other attachment means. Any of these attachment means may be released by, for example, manipulating a trigger wire. Such alternatives are contemplated within the scope of this disclosure.

The prosthesis 10 may be suitable for placement in a location within the vasculature of a patient regardless of whether that particular location requires a prosthesis that is biased to the right or a prosthesis that is biased to the left. For example, the prosthetic branch 40 of the prosthesis 10 may be moved to the right biased configuration for placement in one common iliac artery or moved to the left biased configuration for placement in the other common iliac artery. Thus, the prosthesis 10 may be suitable for placement in either of the common iliac arteries. One advantage of such a prosthesis may be to reduce the need for a clinic to maintain an inventory of multiple devices for placement in the different common iliac arteries.

The prosthetic branch 40 may be moved to the right biased configuration or the left biased configuration by selective release of the left steering member 90 or the right steering member 70, the remaining steering member remaining releasably attached to the prosthetic branch and/or the prosthetic trunk 20. Once the prosthetic branch 40 is in the right or left biased configuration, the remaining steering member may be released from the prosthetic trunk 20 and/or the prosthetic branch to free the second end 43 of the prosthetic branch from the prosthetic trunk. This may enable the prosthetic branch 40 to move to a free configuration as shown in FIGS. 5*a*-5*b*. In the free configuration, the prosthetic branch 40 may be generally aligned with the prosthetic trunk 20. For example, the longitudinal axis of the prosthetic branch 40 and the longitudinal axis of the prosthetic trunk 20 may be substantially coplanar along the plane A. The second end 43 of the prosthetic branch 40 may be spaced from the prosthetic trunk 20 such that the outer surface 47 of the graft body 45 of the prosthetic branch may not be in abutting contact with the outer surface 27 of the graft body 25 of the prosthetic trunk along substantially an entire length of the prosthetic branch extending between the first and second ends 41, 43 thereof.

Figure 6:
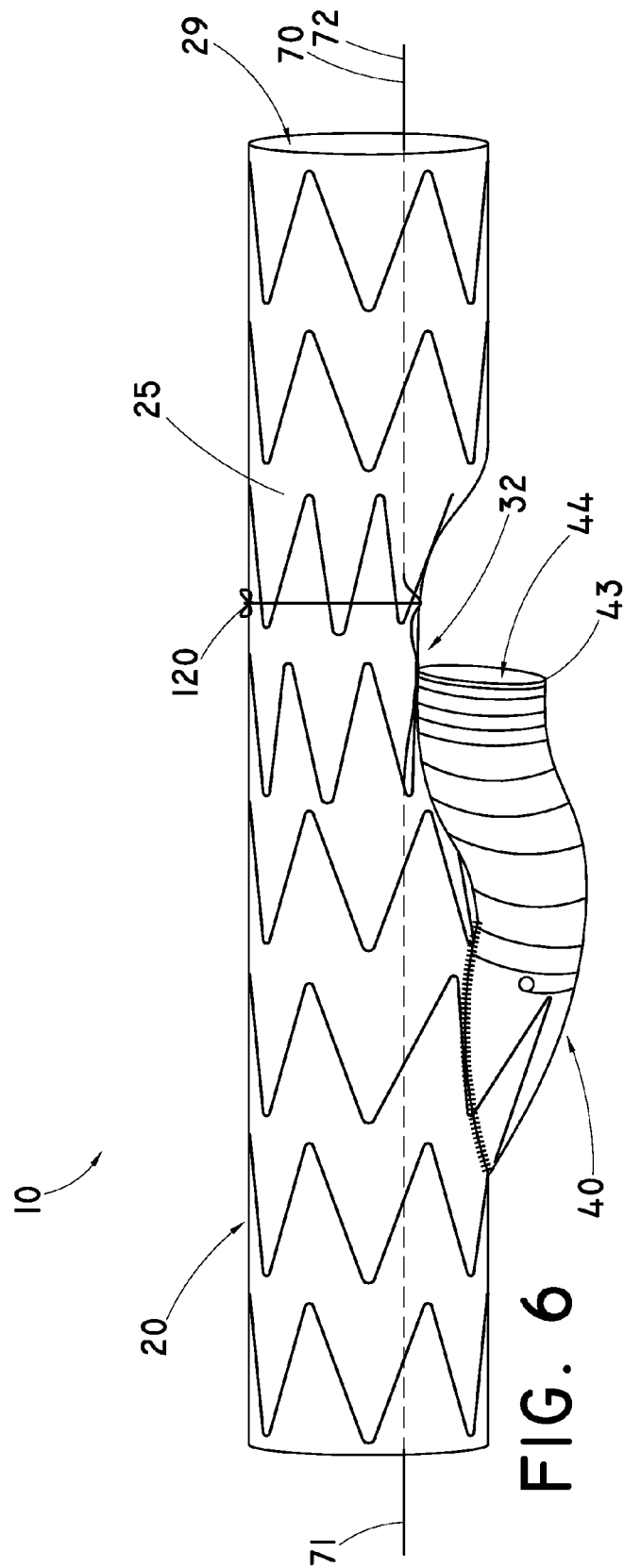
FIG. 6 depicts the prosthesis of FIG. 1 with a diameter reducing tie.

The prosthesis 10 and/or a portion thereof further may be movable between a compressed configuration and an expanded configuration. FIG. 6 depicts the prosthesis 10 with a portion thereof in the compressed configuration. In the compressed configuration, a portion of the prosthetic trunk 20 (e.g., a portion corresponding to a support structure or a portion thereof) proximate the second end 43 of the prosthetic branch 40 may be retained in a compressed state. In other words, a portion of the prosthetic trunk 20 may be compressed such that the diameter of that portion of the prosthetic trunk may be reduced. The compressed portion may be retained in the compressed configuration by one or more diameter reducing ties 120. The diameter reducing ties 120 may surround the graft body 25 of the prosthetic trunk 20 circumferentially at a location proximate the second end 43 of the prosthetic branch 40. The diameter reducing ties 120 may be positioned distal to the second end 43 of the prosthetic branch 40 as shown in FIG. 6. The diameter reducing ties 120 further may be positioned distal of the recess 32 that may be formed in the prosthetic trunk 20 as described herein. The diameter reducing ties 120 may be tightened around the prosthetic trunk 20 to compress a portion thereof to the compressed state. Alternatively, a portion of the prosthetic trunk 20 may be compressed by any means, and the diameter reducing ties 120 may be attached to the prosthetic trunk to retain the compressed portion in the compressed state. The diameter reducing ties 120 may be releasably attached to the prosthetic trunk 20 such that releasing the diameter reducing ties from the prosthetic trunk may enable the compressed portion of the prosthetic trunk to expand from the compressed state, whereby the prosthetic trunk may attain the expanded configuration. The compressed portion of the prosthetic trunk may be allowed to fully expand to the expanded configuration as shown in FIG. 1. In other words, the compressed portion may be allowed to expand, for example under the effect of self expanding stents, to achieve the original diameter of that portion prior to compression.

The diameter reducing ties 120 may help to further reduce the outer diameter of the prosthesis 10 for delivery within the vasculature of the patient. The outer diameter of the prosthesis 10 may be reduced by the diameter reducing ties even after the prosthesis has been deployed from within a delivery device so that the position of the prosthesis may be more easily adjusted prior to complete expansion of the prosthesis to the expanded configuration. The diameter reducing ties further may help to prevent the graft body 25 of the prosthetic trunk 20 from occluding the second end opening 44 of the prosthetic branch 40 when the prosthetic branch is in the neutral configuration. In other words, by retaining a portion of the prosthetic trunk 20 distal of the second end 43 of the prosthetic branch 40 in the compressed state, a space may be maintained between the graft material of the graft body 25 of the prosthetic trunk 20 and the second end opening 44 of the prosthetic branch. The space may enable passage of instruments and/or other prostheses through the prosthetic branch during treatment.

The right steering member 70 and/or the left steering member 90 may be releasably attached to the diameter reducing ties 120 as shown in FIG. 6. The diameter reducing ties 120 may be configured to release from the prosthetic trunk 20 upon retraction of the right and/or left steering member 70, 90. For example, the right steering member 70 may be releasably attached to the diameter reducing ties 120 by threading the right steering member through a portion of the diameter reducing ties. The right steering member 70 may extend generally longitudinally within the trunk lumen 29 as described herein. The right steering member 70 may penetrate the graft body 25 of the prosthetic trunk 20 to exit the trunk lumen 29 at a position proximal to the diameter reducing ties, pass through the diameter reducing ties, and penetrate the graft body of the prosthetic trunk to re-enter the trunk lumen at a position distal to the diameter reducing ties. The first end 71 or the second end 72 of the right steering member 70 may be retracted to steer the prosthetic branch 40 toward the left biased configuration as described herein. The first or second end 71, 72 of the right steering member 70 may be retracted further to release the right steering member from engagement with the diameter reducing ties 120. The diameter reducing ties 120 may be configured such that releasing the right steering member 70 from engagement with the diameter reducing ties may release the diameter reducing ties from the prosthetic trunk 20. In other words, an end of the right steering member 70 may be retracted a first distance to enable the prosthetic branch 40 to move to the left biased configuration and then further retracted a second distance to release the diameter reducing ties 120 from the prosthetic trunk 20. Thus, upon retraction of the first or second end 71, 72 of the right steering member 70, the prosthetic branch 40 first may be allowed to move to the left biased configuration and then the diameter reducing ties 120 may be released from the prosthetic trunk 20 to enable expansion of the prosthetic trunk. Alternatively, the right steering member 70 may be threaded through the diameter reducing ties 120, the prosthetic trunk 20, and/or the prosthetic branch 40 such that, upon retraction of the first or second end 71, 72 of the right steering member, the diameter reducing ties first may be released from the prosthetic trunk and then the prosthetic branch may be allowed to move to the left biased configuration. The left steering member 90 may be releasably attached to the diameter reducing ties in similar fashion with like results. For example, the left steering member 90 may be threaded through the diameter reducing ties 120, the prosthetic trunk 20, and/or the prosthetic branch 40 such that, upon retraction of the first or second end 91, 92 of the left steering member, the prosthetic branch may be allowed to move to the right biased configuration and then the diameter reducing ties may be released from the prosthetic trunk to enable expansion of the prosthetic trunk. The diameter reducing ties 120 may be configured to be released by retraction of the right steering member 70 only, the left steering member 90 only, one of the right and left steering members, or both of the right and left steering members.

The diameter reducing ties 120 may be configured as diameter constricting sutures. In one preferred embodiment, two independent steering trigger wires (i.e. the right and left steering members) are utilized. The wires traverse a delivery system toward a graft (i.e., the prosthesis), exit an end of a positioner, and enter the lumen of the main body (i.e., the prosthetic trunk) from the distal end. The first steering wire (i.e., the right steering member) pierces the graft at ~3:00 approximately 15 mm distal to the distal margin of the branch. The wire passes through a diameter constricting suture, then pierces the graft to re-enter the lumen. The wire then traverses proximally within the lumen of the device to ~4 mm distal of the distal margin of the branch and pierces the graft to exit the lumen. Next, the wire enters the branch from the distal end and traverses ~4 mm within the branch, then pierces it to exit. The wire then pierces the main body to re-enter the lumen, progresses lumenally and exits the proximal end of the device. A second steering wire (i.e., the left steering member) takes the same path as the first wire, but pierces the main body at ~9:00. When both wires are in place, the graft is held with its diameter reduced and the branch at 12:00. As either wire is removed, first the branch turns to bias in the direction of the remaining wire, then when the wire is fully withdrawn, the diameter reducing suture is released and the diameter returns to full size. This allows the physician to give the device bias in either direction, and also allows for improved control and flexibility for cannulation of the branch vessel.

The diameter reducing ties may be any type of filamentary member known in the art. For example, the diameter reducing ties may be lengths of suture material which are fastened to the graft material and are looped around a trigger wire and pulled tight so that the diameter of the prosthetic trunk is reduced. When the trigger wire is released, the loops of the diameter reducing ties are released and the prosthetic trunk can expand to its full size. After release, the diameter reducing ties may remain fixed to the graft material of the prosthetic trunk. The diameter reducing ties may be made of any material known in the art. For example, the diameter reducing ties 120 may be made of any of the materials described herein with reference to the steering members. Examples of diameter reducing ties include those described in U.S. Patent Application Pub. Nos. 2004/0098084, 2008/0114438, and 2009/0254170 by Hartley et al., which are incorporated by reference herein in their entirety. The diameter reducing ties 120 also may be configured as a clip, sleeve, ring, coil, or any other configuration capable of retaining a portion of the prosthetic trunk in the compressed configuration.

Figure 7:
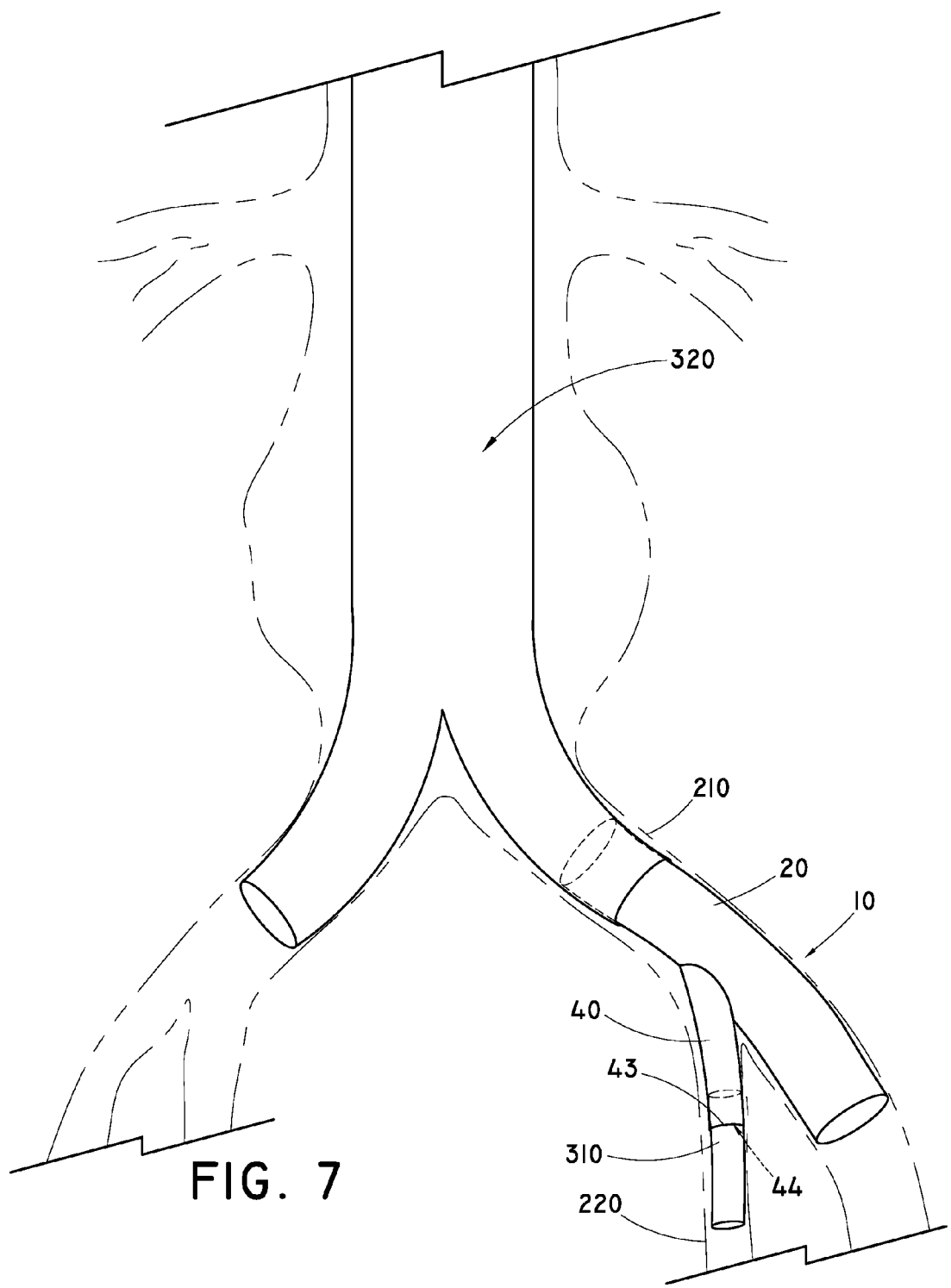
FIG. 7 depicts the prosthesis of FIG. 1 deployed in an iliac artery.

FIG. 7 depicts the prosthesis 10 deployed within the vasculature of a patient. The prosthesis 10 may be deployed, for example, in a common iliac artery 210 such that the prosthetic branch 40 may be aligned with an internal iliac artery 220. The prosthesis 10 may be deployed using standard endoluminal techniques. For example, the prosthesis 10 may be deployed using the devices and/or methods described in U.S. Pat. Nos. 7,435,253 to Hartley et al. and 7,407,509 to Greenberg et al., which are incorporated by reference herein in their entirety.

The prosthesis 10 may be compressed into a delivery configuration and loaded into a delivery device, such as an introducer or sheath. The right and left steering members 70, 90 may extend generally longitudinally within the delivery device. The second ends 72, 92 of the right and left steering members 70, 90 may be attached to one or more control mechanisms at the distal end of the delivery device. Manipulation of the control mechanism may cause the second end 72 of the right steering member 70 and/or the second end 92 of the left steering member 90 to release from the prosthetic branch 40 and/or the prosthetic trunk 20 (e.g., by retracting the respective end) to steer the prosthetic branch as described herein. The right and left steering members may extend through the second end opening 24 of the prosthetic trunk 20 and proximally through the trunk lumen 29 as shown in FIG. 2*a*. The right and left steering members 70, 90 may be threaded through the prosthetic trunk 20 and/or the prosthetic branch 40 as described herein to releasably attach the prosthetic branch to the prosthetic trunk to retain the prosthetic branch in the neutral configuration. The right and left steering members 70, 90 may extend further proximally within the trunk lumen 29 and through the first end opening 22 of the prosthetic trunk 20. The first ends 71, 91 of the right and left steering members 70, 90 may be releasably attached to a proximal tip of the delivery device. In this manner, the right and left steering members may be releasably attached to the distal and proximal ends of the delivery device and threaded through the prosthetic trunk and/or the prosthetic branch to retain the prosthetic branch in the neutral configuration for delivery within the vasculature.

The proximal tip of the delivery device may be introduced within the vasculature of the patient using known means and navigated to a treatment site therein. For example, the proximal tip of the delivery device may be introduced into the femoral artery of the patient and navigated to a position proximate the common iliac bifurcation. The prosthesis 10 may be deployed by, for example, retracting a sheath of the delivery device to enable expansion of the prosthesis. Upon deployment, the prosthesis 10 may expand to the deployed configuration. Once the prosthesis 10 has been positioned, the control mechanism of the delivery device may be manipulated to release the first end 71, 91 of the right or left steering member 70, 90 from the proximal tip of the delivery device and/or to retract the second end 72, 92 of the right or left steering member to steer the prosthetic branch 40 to the right biased configuration, as shown in FIGS. 3*a*-3*b*, or the left biased configuration, as shown in FIGS. 4*a*-4*b*. In this manner, the prosthesis 10 may be positioned such that the prosthetic trunk 20 may be disposed in the common iliac artery 210 and the second end opening 44 of the prosthetic branch 40 may be aligned with the branching vessel 220, such as an internal iliac artery as shown in FIG. 7.

Additional instruments (e.g., a guide wire or a second delivery device) may be introduced within the prosthesis 10. For example, the second delivery device may be introduced within the branch lumen 49 of the prosthetic branch 40. The second delivery device may extend between the branch lumen 49 of the prosthetic branch 40 and a lumen of the branching vessel 220 to maintain the prosthetic branch 40 in alignment with the branching vessel. The remaining right or left steering member 70, 90 may be removed to free the second end 43 of the prosthetic branch 40 from the prosthetic trunk 20. The second delivery device may maintain the prosthetic branch 40 in alignment with the branching vessel 220 upon release of the remaining steering member. In other words, the prosthetic branch may be prevented from moving to the free configuration (i.e., aligning with the prosthetic trunk 20) by the second delivery device extending therethrough. A second prosthesis 310, such as a stent graft, may be deployed using the second delivery device to bridge a space between the second end 43 of the prosthetic branch 40 and the branching vessel 220. Additional prostheses (e.g., a bifurcated stent graft 320) may be deployed in similar fashion to bridge aneurysmal portions of the vasculature as is known in the art. In one example, the prosthesis 10 may be integral with the bifurcated stent graft 320. In other words, one leg of the stent graft 320 (e.g., an ipsilateral leg) may include the prosthesis 10. The unitary bifurcated stent graft may include the branch 40, which may be steerable as described herein.

In one example, a method of steering a prosthetic branch between a neutral configuration and one of a first biased configuration or a second biased configuration may include providing a prosthesis comprising a prosthetic trunk and a prosthetic branch. A first end of the prosthetic branch may be attached to the prosthetic trunk, and a second end of the prosthetic branch may be releasably attached to the prosthetic trunk by first and second steering members. The method may include selectively releasing one of the first or second steering members from the prosthetic branch or the prosthetic trunk to enable the prosthetic branch to move to the second biased configuration or the first biased configuration, respectively. The releasing step may include retracting an end of the respective first steering member or second steering member to unthread the steering member from a graft body of the prosthetic trunk. The method may include releasing the respective first steering member or second steering member from at least one diameter reducing tie to enable a portion of the prosthetic trunk to expand from a compressed configuration. Releasing the respective first or second steering member from the prosthetic branch may include retracting an end of the steering member a first distance to unthread the steering member from a graft body of the prosthetic branch, and releasing the respective first or second steering member from the diameter reducing tie may include retracting the end of the steering member a second distance to unthread the steering member from the diameter reducing tie.

It can be appreciated by those skilled in the art that specific features of each embodiment of the device may be interchangeable among the various embodiments, even where no references to the specific features are made. Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including features described with respect to different embodiments, and may be combined with each other and/or with currently-known or future-developed technologies while remaining within the scope of the claims presented herein. It is therefore intended that the foregoing detailed description be regarded as illustrative rather than limiting. And it should be understood that the following claims, including all equivalents, are intended to define the spirit and scope of this invention.

We claim:

1. An endoluminal prosthesis comprising:
a prosthetic trunk comprising a tubular graft body, an open first end, an open second end, and a trunk lumen in fluid communication with the first end and the second end of the prosthetic trunk;
a prosthetic branch comprising a tubular graft body, an open first end, an open second end, and a branch lumen in fluid communication with the first end and the second end of the prosthetic branch, the first end of the prosthetic branch joined to an intermediate portion of the prosthetic trunk, the branch lumen in fluid communication with the trunk lumen, the prosthetic branch extending from the prosthetic trunk and being movable with respect to the prosthetic trunk between a neutral configuration wherein the prosthetic branch is substantially aligned with the prosthetic trunk, a first biased configuration wherein the second end of the prosthetic branch extends away from the prosthetic trunk in a first direction to a first side of the prosthetic trunk, and a second biased configuration wherein the second end of the prosthetic branch extends away from the prosthetic trunk in a second direction to a second side of the prosthetic trunk opposite the first side; and a first releasable steering member associated with the first biased configuration and a second releasable steering member associated with the second biased configuration, the steering members cooperatively retaining the prosthetic branch in the neutral configuration;

wherein, upon release of one of the first steering member or the second steering member from the prosthetic branch, the prosthetic branch moves into one of the first biased configuration or the second biased configuration.

2. The prosthesis of claim 1, wherein each of the first steering member and the second steering member is releasably attached to the prosthetic trunk and the second end of the prosthetic branch and is independently releasable to release at least a portion of the second end of the prosthetic branch from the prosthetic trunk, and wherein each of the first steering member and the second steering member, when attached, produces a counter tension upon the prosthetic branch to cooperatively retain the prosthetic branch in the neutral configuration.

3. The prosthesis of claim 2, wherein each of the first steering member and the second steering member penetrates the body of the prosthetic trunk at a first longitudinal position proximal to the second end of the prosthetic branch and a second longitudinal position distal to the second end of the prosthetic branch, an external segment of the respective steering member is positioned between the first longitudinal position and the second longitudinal position, and the external segment of each of the first steering member and the second steering member penetrates the body of the prosthetic branch and extends through the open second end of the prosthetic branch to releasably attach the second end of the prosthetic branch to the prosthetic trunk.

4. The prosthesis of claim 2, wherein the first releasable steering member is releasably attached to the prosthetic trunk at a first circumferential position on the first side of the prosthetic trunk, and the second releasable steering member is releasably attached to the prosthetic trunk at a second circumferential position on the second side of the prosthetic trunk.

5. The prosthesis of claim 1, wherein, in the neutral configuration, at least a portion of the prosthetic branch is received within a recess in the prosthetic trunk.

6. The prosthesis of claim 1, wherein release of one of the first steering member or the second steering member from at least one of the prosthetic trunk or the prosthetic branch partially releases the second end of the prosthetic branch from the prosthetic trunk to enable the second end of the prosthetic branch to move relative to the prosthetic trunk in the direction of the other of the first steering member or the second steering member.

7. The prosthesis of claim 1, wherein at least one of the first steering member or the second steering member penetrates the graft body of the prosthetic branch and the graft body of the prosthetic trunk through self-sealing portions thereof.

8. The prosthesis of claim 1, wherein a longitudinal segment of the prosthetic trunk near the second end of the prosthetic branch is retained in a compressed configuration.

9. The prosthesis of claim 8, wherein the graft body of the longitudinal segment of the prosthetic trunk in the compressed configuration is longitudinally spaced from the open second end of the prosthetic branch.

10. An endoluminal prosthesis comprising:
a prosthetic trunk comprising a tubular graft body, an open first end, an open second end, and a trunk lumen extending between the first end and the second end of the prosthetic trunk;
a prosthetic branch comprising a tubular graft body, an open first end, an open second end, and a branch lumen extending between the first end and the second end of the prosthetic branch, the first end of the prosthetic branch joined to the prosthetic trunk, the branch lumen in fluid communication with the trunk lumen, and the prosthetic branch extending outward from the prosthetic trunk;
a first releasable steering member releasably attached to the second end of the prosthetic branch at a first circumferential position and to the prosthetic trunk at a second circumferential position on a first side of the prosthetic trunk; and
a second releasable steering member releasably attached to the second end of the prosthetic branch at a third circumferential position and to the prosthetic trunk at a fourth circumferential position on a second side of the prosthetic trunk opposite the first side, the first releasable steering member and the second releasable steering member cooperatively maintaining the prosthetic branch in a neutral configuration in which the prosthetic branch is substantially aligned with the prosthetic trunk.

11. The prosthesis of claim 10, wherein the first circumferential position and the third circumferential position are spaced from one another with respect to a circumference of the prosthetic branch, and the second circumferential position and the fourth circumferential position are spaced from one another with respect to a circumference of the prosthetic trunk.

12. The prosthesis of claim 10, wherein, in the neutral configuration, the first circumferential position of the prosthetic branch is in contact with the second circumferential position of the prosthetic trunk, and the third circumferential position of the prosthetic branch is in contact with the fourth circumferential position of the prosthetic trunk.

13. The prosthesis of claim 10, wherein, upon release of one of the second steering member or the first steering member, the prosthetic branch is movable with respect to the prosthetic trunk between the neutral configuration and a respective one of a first biased configuration in which the prosthetic branch extends longitudinally and transversely relative to the prosthetic trunk in a first direction to the first side of the prosthetic trunk and a second biased configuration in which the prosthetic branch extends longitudinally and transversely relative to the prosthetic trunk in a second direction to the second side of the prosthetic trunk.

14. The prosthesis of claim 13, wherein, upon release of the second steering member, the prosthetic branch moves into the first biased configuration, the first circumferential position of the prosthetic branch is in contact with the second circumferential position of the prosthetic trunk, and the third circumferential position of the prosthetic branch is spaced from the fourth circumferential position of the prosthetic trunk.

15. The prosthesis of claim 10, further comprising at least one diameter reducing tie releasably attached to the prosthetic trunk, the diameter reducing tie engaging the graft body of the prosthetic trunk to retain a portion of the prosthetic trunk in a compressed configuration.

16. The prosthesis of claim 15, further comprising a space positioned between the graft body of the compressed portion of the prosthetic trunk and the open second end of the prosthetic branch.

17. The prosthesis of claim 10, wherein each of the first steering member and the second steering member is threaded through the graft body of the prosthetic branch and the graft body of the prosthetic trunk to releasably attach the second end of the prosthetic branch to the prosthetic trunk.

18. The prosthesis of claim 17, further comprising at least one diameter reducing tie releasably attached to the prosthetic trunk, the diameter reducing tie engaging the graft body of the prosthetic trunk to retain a portion of the prosthetic trunk in a compressed configuration, wherein at least one of the first steering member or the second steering member is releasably attached to the diameter reducing tie, and the diameter reducing tie is released from the prosthetic trunk upon release of the respective first or second steering member from the diameter reducing tie.

19. The prosthesis of claim 10, wherein each of the first steering member and the second steering member penetrates the body of the prosthetic trunk at a first longitudinal position proximal to the second end of the prosthetic branch and a second longitudinal position distal to the second end of the prosthetic branch, an external segment of the respective steering member is positioned between the first longitudinal position and the second longitudinal position, and the external segment of each of the first steering member and the second steering member penetrates the body of the prosthetic branch and extends through the open second end of the prosthetic branch to releasably attach the second end of the prosthetic branch to the prosthetic trunk.

* * * * *